US011234414B2

(12) United States Patent
Vasconcelos

(10) Patent No.: US 11,234,414 B2
(45) Date of Patent: Feb. 1, 2022

(54) ANIMAL MARKING SYSTEM

(71) Applicant: Robert Bosch Limitada, Campinas-SP (BR)

(72) Inventor: Alvaro Augusto Vasconcelos, Campinas-SP (BR)

(73) Assignee: Robert Bosch Limitada, Campinas-SP (BR)

( * ) Notice: Subject to any disclaimer, the term of this patent is extended or adjusted under 35 U.S.C. 154(b) by 118 days.

(21) Appl. No.: 16/004,525

(22) Filed: Jun. 11, 2018

(65) Prior Publication Data

US 2018/0368360 A1 Dec. 27, 2018

(30) Foreign Application Priority Data

Jun. 27, 2017 (BR) .................. BR102017013887-9

(51) Int. Cl.
| | |
|---|---|
| *A01K 11/00* | (2006.01) |
| *A01K 13/00* | (2006.01) |
| *B05B 1/14* | (2006.01) |
| *A61B 90/00* | (2016.01) |
| *B65D 83/26* | (2006.01) |
| *G09F 21/02* | (2006.01) |

(52) U.S. Cl.
CPC ............. *A01K 11/00* (2013.01); *A01K 13/00* (2013.01); *A61B 90/39* (2016.02); *B05B 1/14* (2013.01); *B65D 83/262* (2013.01); *A61B 2090/395* (2016.02); *A61B 2090/3933* (2016.02); *A61B 2503/40* (2013.01); *G09F 21/02* (2013.01)

(58) Field of Classification Search
CPC .... A01K 11/00; A01K 11/005; A01K 11/006; A01K 13/001; A01K 13/003; A01K 35/00; B05B 3/00; B05B 1/14; B65D 83/14; B65D 83/262; A61B 90/39; A61B 2090/3933; A61B 2090/395
USPC ..................... 239/DIG. 14, 14; 222/645–648
See application file for complete search history.

(56) References Cited

U.S. PATENT DOCUMENTS

| | | | | |
|---|---|---|---|---|
| 3,173,402 | A * | 3/1965 | Cassel .................. | A01K 13/003 119/667 |
| 4,440,078 | A * | 4/1984 | McCrery, Jr. ........ | A01K 11/005 101/26 |
| 5,790,047 | A * | 8/1998 | Golan .................. | A01K 11/006 340/10.42 |
| 6,901,885 | B1 * | 6/2005 | Kleinsasser .......... | A01K 11/005 119/842 |

(Continued)

FOREIGN PATENT DOCUMENTS

CN             204929952 U       1/2016

*Primary Examiner* — Robert A Lynch
(74) *Attorney, Agent, or Firm* — Michael Best & Friedrich LLP

(57) ABSTRACT

The invention relates to an animal marking system (1) provided with a drive device (10) and an animal marking fluid sprayer (2), the drive device (10) comprising an electric motor (11) associated with a transmission system (12), the transmission system receiving an initial torque from the electric motor (11), amplifying the received initial torque and transmitting the amplified torque to a drive shaft (3), the drive shaft (3) applying the amplified torque to actuate the animal marking fluid sprayer (2), the animal marking system (1) being able to be applied in extensive rural territory, where there is not a wide availability to use mechanisms that require high drive voltages.

9 Claims, 4 Drawing Sheets

(56) References Cited

U.S. PATENT DOCUMENTS

| | | | | |
|---|---|---|---|---|
| 8,061,562 B2 * | 11/2011 | Carpenter | ............... | B05B 12/12 |
| | | | | 222/52 |
| 10,132,673 B1 * | 11/2018 | Eakin | .................... | A01K 11/005 |
| 10,473,514 B1 * | 11/2019 | Ostermann | ............ | G01G 23/40 |
| 2004/0144333 A1 * | 7/2004 | Finlayson | ............ | A01K 11/007 |
| | | | | 119/858 |
| 2006/0275555 A1 * | 12/2006 | Colizza | .................. | B05B 5/053 |
| | | | | 427/458 |
| 2013/0322699 A1 * | 12/2013 | Spicola, Sr. | ............. | G01G 9/00 |
| | | | | 382/110 |
| 2018/0220617 A1 * | 8/2018 | Avila | ....................... | A61D 7/00 |

* cited by examiner

ANIMAL MARKING SYSTEM

BACKGROUND OF THE INVENTION

The present invention relates to an animal marking system having a drive device comprising a low voltage drive means applicable in extended rural territory where there is not a wide availability for the use of mechanisms requiring high drive voltages.

Bovine confinement farms are characterized by containing containment bays and at least one corral. A typical farm has between 10 and 12 bays. On the other hand, large farms can contain hundreds of bays. Each bay, in turn, receives between 100 and 150 animals, in three fattening cycles, that is, new animals are admitted in the farm at least three times a year. Thus, large breeders can manage a stock containing from 3,000 to 100,000 different animals per year.

One of the problems associated with the management of large herds is the need to locate, from a distance, different animals that are ideal for slaughter or underweight, or even animals that require medical treatment or specific feeding.

To that end, there are, in the state of the art, marking systems associated with weighing systems and/or animal management systems, comprising paint and/or spray devices, capable of leaving a mark visible on the animal according to its weight and/or treatment to be applied.

For instance, document U.S. Pat. No. 5,790,047 describes a system and method for marking an animal with a visible marking indicative of a treatment to be performed which uses an identification code to remotely identify the animal and access a database containing the specific information of the identified animal. The system comprises a paint spray station, through which the animal passes and is marked with different colors, according to the treatment to be performed.

In another example, document CN204929952 describes an automatic animal marking device comprising support means for a paint spray and an electromagnetic drive means for enabling the application of said paint spray. The electromagnetic drive means comprises a power supply circuit utilizing a DC power source.

However, most of the marking systems found in the state of the art require an auxiliary pump and/or an additional paint reservoir, as is the case of the system described in U.S. Pat. No. 5,790,047, making its use impossible for the confinement of beef cattle, mainly due to the high cost of both the apparatus itself and the cost of the provision of electric energy to drive the auxiliary pump.

On the other hand, the system described by CN204929952 uses a solenoid drive means which controls a drive spring, which in turn directly drives a drive shaft of the paint spray. Therefore, the solenoid must be sized to provide the torque required to drive the spray directly, that is, without the use of a torque multiplication system. The strength of the solenoid is proportional to its drive voltage, so that approximately 100 V (Volts) of voltage is required for its drive. However, the use of a voltage of 100 V is not feasible for field application, since these voltage quantities are not widely available.

SUMMARY OF THE INVENTION

The aim of the present invention is to provide an animal marking system having a drive device comprising a low voltage drive means, between 2 Volts and 14 Volts, the drive means providing a reduced initial torque, which is enlarged by means of a transmission system associated with the drive means, so that the enlarged torque is capable of driving a drive shaft which actuates a spray mechanism of a marking fluid.

The aim of the present invention is achieved by an animal marking system provided with a drive device and a fluid sprayer for animal marking, the drive device comprising an electric motor associated with a transmission system, the transmission system receiving an initial torque from the electric motor, increasing the initial torque received and transmitting the amplified torque to a drive shaft, the drive shaft applying the extended torque to actuate the fluid sprayer for animal marking, the electric motor comprising a voltage between 2 V and 14 V, preferably comprising a voltage of 3 V, the transmission system amplifying the initial torque supplied by the electric motor by means of a plurality of gears, the animal marking fluid sprayer being configured by a paint spray, with the marking system being selectively driven by the steel drive device with information received from animal management, weighing and identification systems.

BRIEF DESCRIPTION OF THE DRAWINGS

A more detailed description of the instant invention follows, based on one embodiment represented in the drawings. The figures show.

DETAILED DESCRIPTION

The animal marking system 1 of the present invention is selectively driven by a drive device 10, according to the information received from a weighing system associated with an identification system and an animal management system. The animal is weighed by the weighing system and identified by the identification system, so that the animal's weight and identification information is transmitted to the management system. The management system comprises a database containing information specific to the animal and is able to determine the need to perform some type of visual marking on the particular animal.

If the animal is at the ideal slaughter weight, the management system transmits information to the drive device 10 of the marking system 1, which sprays a first colored paint, for example a green paint, onto the animal's back. If it is identified that a given animal is underweight, the management system transmits the information to the drive device 10 of the marking system 1, which sprays a second colored paint, for example a red paint, indicating that the needs specific care.

The management system is also able to identify if an animal needs a specific treatment, such as a vaccination treatment. In this case, the marking system 1 uses a third colored paint, for example a yellow paint, indicating that the animal needs other care that is not related to its weight.

The animal marking system 1 comprises from a single spray mechanism 2 to a plurality of spray mechanisms, according to the need of each design.

Figures 1, 2:
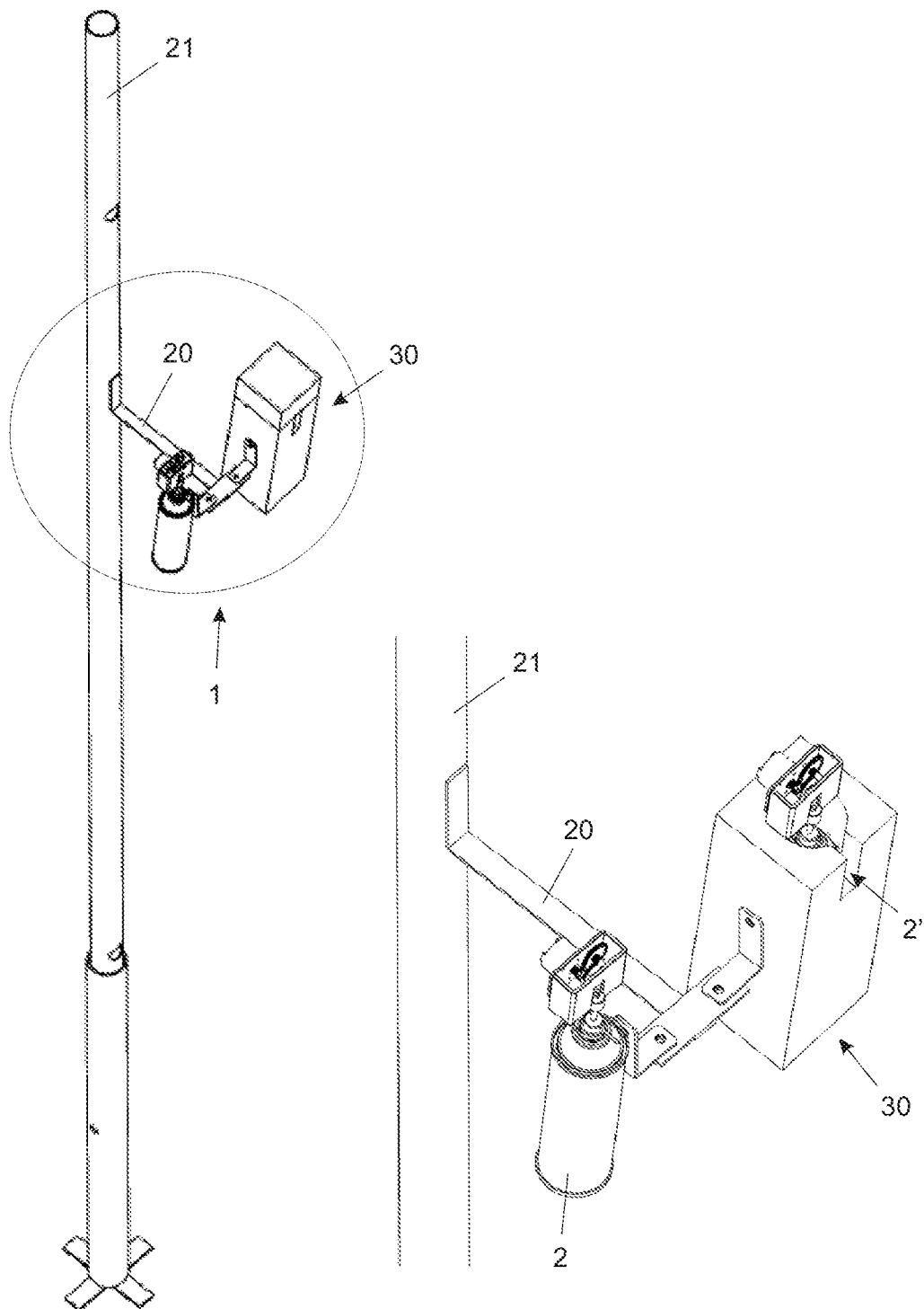
FIG. 1—a perspective view of a mounting and fastening assembly of the animal marking system of the present invention.
FIG. 2—a detailed perspective view of the mounting and fastening assembly of the animal marking system of the present invention.

FIG. 1 shows an alternative mounting and fastening assembly of the animal marking system 1 of the present invention, which is fastened to an arm projection 20 associated with a pole/mast 21, at a height sufficient to spray the animal marking fluid in a visible position on the animal's back.

In the alternative illustrated in FIG. 1, the animal marking system 1 preferably comprises, but not necessarily, two sprayers 2, 2'. In alternative configurations, the animal marking system 1 comprises only one sprayer or a plurality of sprayers, whether they are 3, 4, 5, 6, 7, 10 or more sprayers. The animal marking fluid sprayer 2, 2' includes one or more paint sprays.

Each sprayer 2 comprises its own drive device 10 and is mounted within a protective housing or a protective box in the form of a shield box 30, as shown in FIGS. 1 and 2. The shield box 30 comprises a preferred, but not mandatory, rectangular-shaped box provided with a body portion 31, on which the sprayer 2 is inserted, and a cover portion 32 closing the shield box 30 and protecting the drive device 10.

Figure 3:
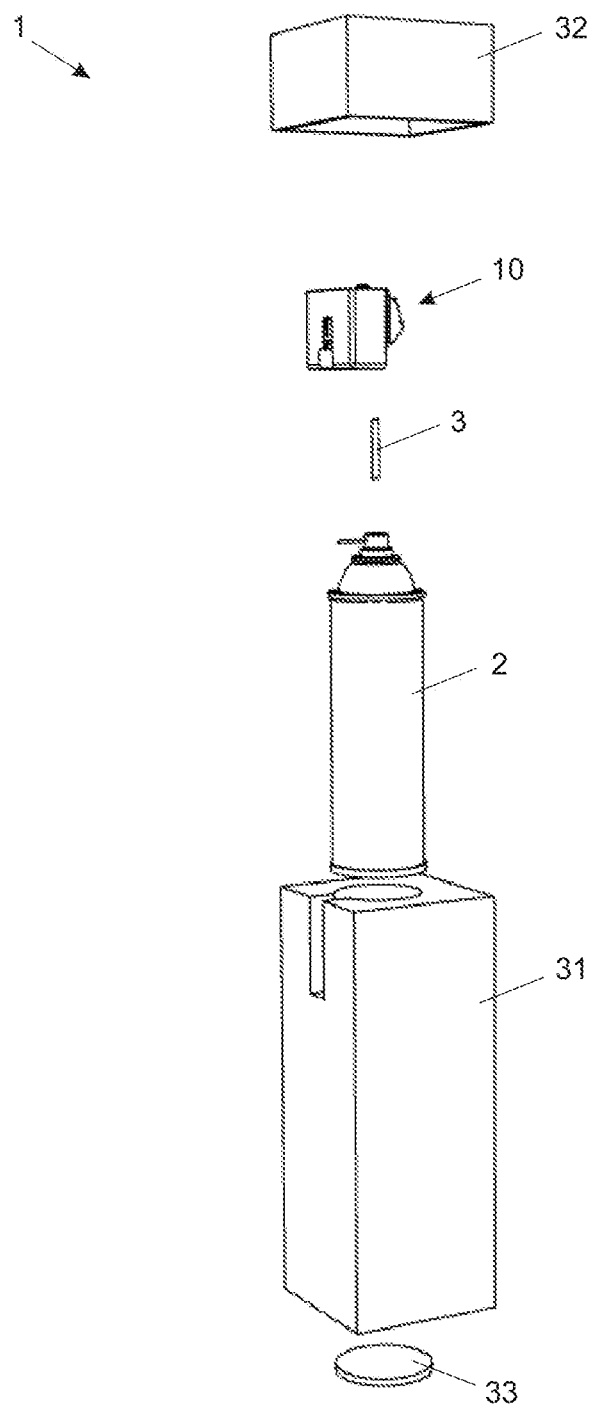
FIG. 3—an exploded perspective view of the animal marking system of the present invention.

FIG. 3 illustrates the animal marking system 1 of the present invention in an exploded view, in which it is possible to observe the shield box 30 with its body portion 31 and cover portion 32, in addition to a bottom portion 33, the sprayer 2, the drive device 10 and a drive shaft 3, which is associated with the drive device 10.

FIGS. 4 to 7 show in detail the drive device 10 provided in the animal marking system 1 of the present invention.

The drive device 10 comprises an electric motor 11, particularly a low voltage electric motor, which is associated with a transmission system 12.

The transmission system 12 receives an initial torque from the electric motor 11 and amplifies the initial torque received, transmitting high torque to the drive shaft 3 which acts on the sprayer 2.

It should be noted that the torque/force provided by the electric motor 11 is proportional to its drive voltage. Thus, a low voltage electric motor provides reduced initial torque which is not sufficient to actuate the fluid sprayer 2 for animal marking.

For this reason, the transmission system 12 which receives the reduced initial torque is used and is capable of extending it sufficiently to generate sufficient force for actuation of the atomizer 2.

Preferably, but not necessarily, the transmission system 12 comprises an assembly of a plurality of gears 13, 14, 15, 16 that are associated to magnify the initial torque provided by the electric motor 11.

The electric motor 11 is of alternating current and comprises a voltage between 2 V (Volts) and 14 V, preferably a voltage of 3 V, and receives energy by means of batteries, there being no need to supply power through a network power.

Figure 4:
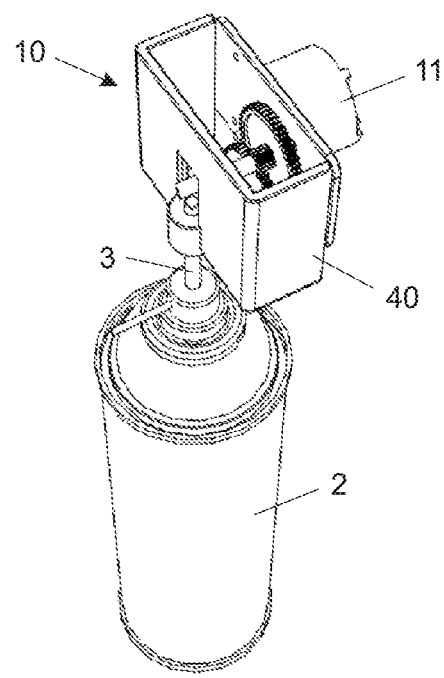
FIG. 4—a perspective view of the animal marking system of the present invention.

In FIG. 4, the drive device 10 is shown in its complete assembly comprising a type of transmission case 40, within which the transmission system 12 is mounted.

Figure 5:
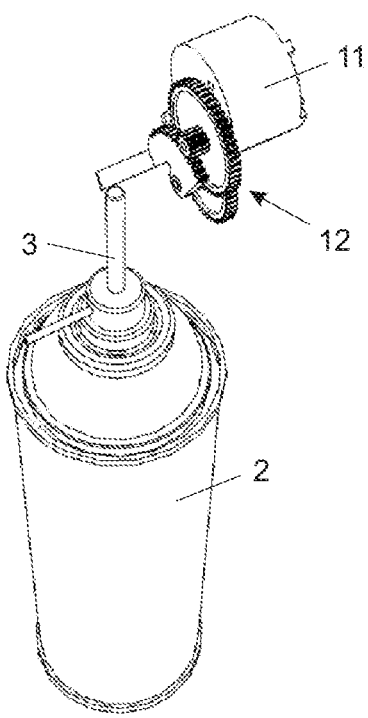
FIG. 5—a perspective view of the animal marking system of the present invention.

In turn, FIG. 5 shows the drive device 10 assembled, but without the transmission case 40, so that it is possible to observe the transmission system 12 assembled and associated with the electric motor 11.

Figure 6:
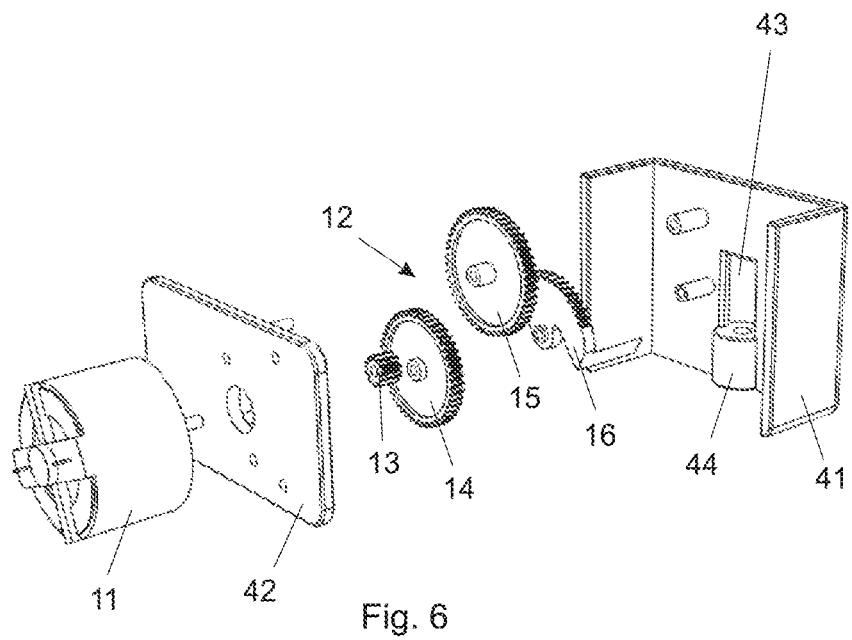
FIG. 6—an exploded perspective view of the drive device of the animal marking system of the present invention.
Figure 7:
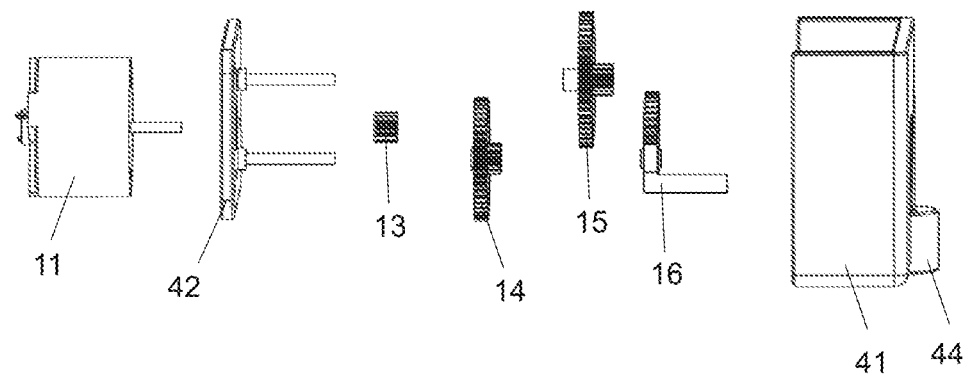
FIG. 7—an exploded side view of the drive device of the animal marking system of the present invention.

Further, FIGS. 6 and 7 show the drive device 10 in exploded views, where it is observed that the transmission box 40 is formed by two parts, one body part 41 and one cover part 42, so that the body part 41 comprises a slot 43 and a cylindrical portion 44, in which the drive shaft 3 is mounted.

The transmission system 12 comprises, preferably but not necessarily, four gears 13, 14, 15, 16. Alternatively, the transmission system 12 comprises 2 or 3 or 5 or 6 or 10 or any amount of gears, provided sufficient to extend the initial torque provided by the electric motor 11 to the torque required for actuation of the sprayer 2.

The drive device 10 is provided in the animal marking fluid sprayer 2 itself, with no need for an auxiliary pump or additional reservoir, being monitored for the amount of use of the paint.

Although one preferred embodiment has been described, it must be understood that the scope of the instant invention covers other possible variations and that it is limited only by the content of the claims, the possible equivalents being included therein.

What is claimed is:

1. An animal marking system (1) configured to communicate with a weighing system for determining a weight of an animal, the animal marking system (1) comprising a drive device (10) and with an animal marking fluid sprayer (2), wherein the drive device (10) comprises an electric motor (11) associated with a transmission system (12), the transmission system (12) receiving an initial torque from the electric motor (11), amplifying the received initial torque and transmitting the amplified torque to a drive shaft (3), applying the amplified torque to actuate the animal marking fluid sprayer (2), wherein the animal marking system (1) further comprises a pole/mast (21) having an arm projection (20) extending from the pole/mast (21), the arm projection (20) supporting the drive device (10) and the animal marking fluid sprayer (2,2') in spaced-apart relation from the pole/mast (21), wherein the pole/mast (21) elevates the animal marking fluid sprayer (2,2') to a height sufficient to spray an animal marking fluid in a visible position on a back of the animal, and wherein the animal marking system (1) includes a rectangular-shaped shield box (30) having a body portion (31), in which the animal marking fluid sprayer (2) is inserted, and a cover portion (32) closing the rectangular-shaped shield box (30) and protecting the drive device (10),
   wherein the animal marking fluid sprayer (2) is configured to mark the animal with the animal marking fluid based on the weight of the animal, and
   wherein the rectangular-shaped shield box (30) includes a bottom wall (33) configured to be removed to provide access to the animal marking fluid sprayer (2).

2. The animal marking system (1) according to claim 1, wherein the electric motor (11) comprises a voltage between 2 V and 14 V.

3. The animal marking system (1) according to claim 1, wherein the electric motor (11) comprises a voltage of 3 V.

4. The animal marking system (1) according to claim 1, wherein the transmission system (12) extends the initial torque provided by the electric motor (11) by means of a plurality of gears (13, 14, 15, 16).

5. The animal marking system (1) according to claim 1, wherein the animal marking fluid sprayer (2) comprises a paint spray.

6. The animal marking system (1) according to claim 1, wherein the arm projection (20) supports a second animal marking fluid sprayer (2,2').

7. The animal marking system (1) according to claim 1, wherein the animal marking fluid sprayer (2) is housed in a longitudinal recess of the rectangular-shaped shield box (30),
- wherein the transmission system (12) is housed in a transmission box (40), and
- wherein the body portion (31) of the rectangular-shaped shield box (30) and the cover portion (32) define a chamber in which the transmission box (40) is housed.

8. The animal marking system (1) according to claim 1, wherein the animal marking fluid sprayer (2) is configured to selectively mark the animal with the animal marking fluid based on the weight of the animal.

9. The animal marking system (1) according to claim 8, wherein the animal marking fluid sprayer (2) is configured to selectively mark the animal with a first color of the animal marking fluid if the weight of the animal is below a threshold weight and with a second color of the animal marking fluid if the weight of the animal is above the threshold weight.

* * * * *